United States Patent [19]

Ohno

[11] Patent Number: 4,840,176

[45] Date of Patent: Jun. 20, 1989

[54] TREATING INSTRUMENT FOR USE WITH AN ENDOSCOPE

[75] Inventor: Kunio Ohno, Tokyo, Japan

[73] Assignee: Olympus Optical Co., Ltd., Tokyo, Japan

[21] Appl. No.: 116,448

[22] Filed: Nov. 3, 1987

[30] Foreign Application Priority Data

Nov. 6, 1986 [JP] Japan .................. 61-264410

[51] Int. Cl.⁴ .............................. A61B 17/36
[52] U.S. Cl. ................. 128/303.14; 128/303.15; 128/328
[58] Field of Search .......... 128/303.14, 303.15, 128/305, 328

[56] References Cited

U.S. PATENT DOCUMENTS 4,190,042 2/1980 Sinnreich .
4,294,254 10/1981 Chamness .
4,602,633 7/1986 Goodfriend et al. ............ 128/328

FOREIGN PATENT DOCUMENTS 46-23833 8/1971 Japan .
52-40616 9/1977 Japan .
54-63989 5/1979 Japan .
56-63348 5/1981 Japan .

Primary Examiner—John D. Yasko
Attorney, Agent, or Firm—Ladas & Parry

[57] ABSTRACT

A treating instrument for use with an endoscope, which has a flexible sheath and an opening at the distal end portion of the sheath. A treating element having directionality is accommodated slidably in the sheath. This treating element is capable of extending through the opening of the sheath to reach the part to be treated from specific directions. An elongated member is connected at one end portion to the proximal end portion of the treating element and inserted slidably in the sheath. Operating member for moving forward and backward and rotating the treating element is attached to the other end portion of the elongated member and is arranged at the rear of the proximal end portion of the sheath. This treating instrument is provided with stopping member for limiting the rotating angle of the treating element when the treating element is rotated by means of the operating member.

17 Claims, 4 Drawing Sheets

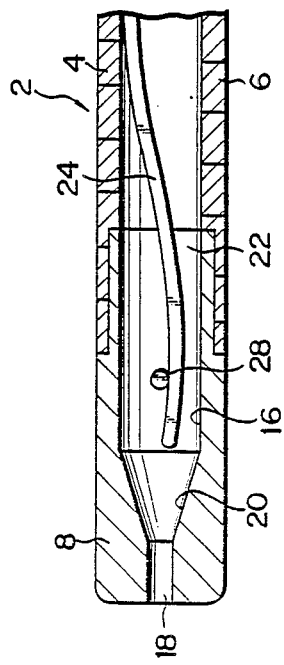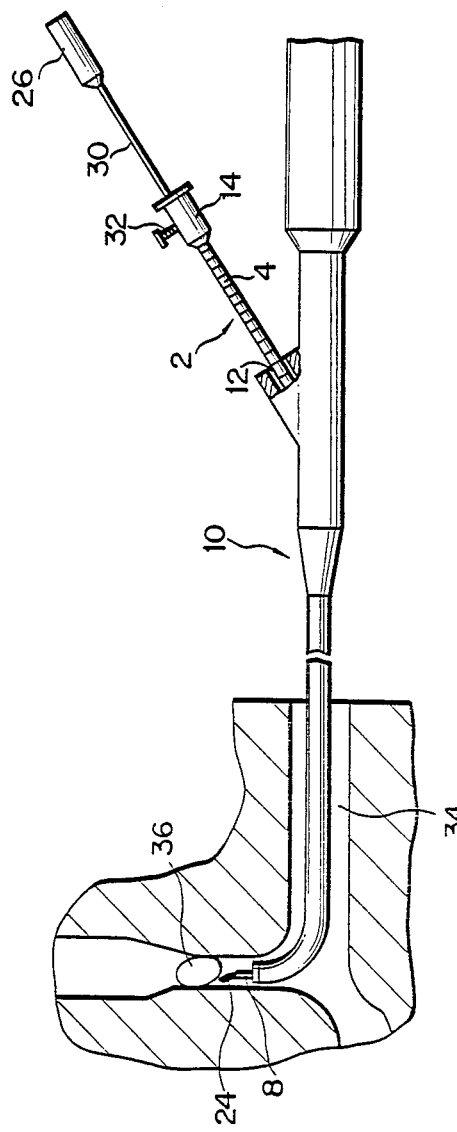

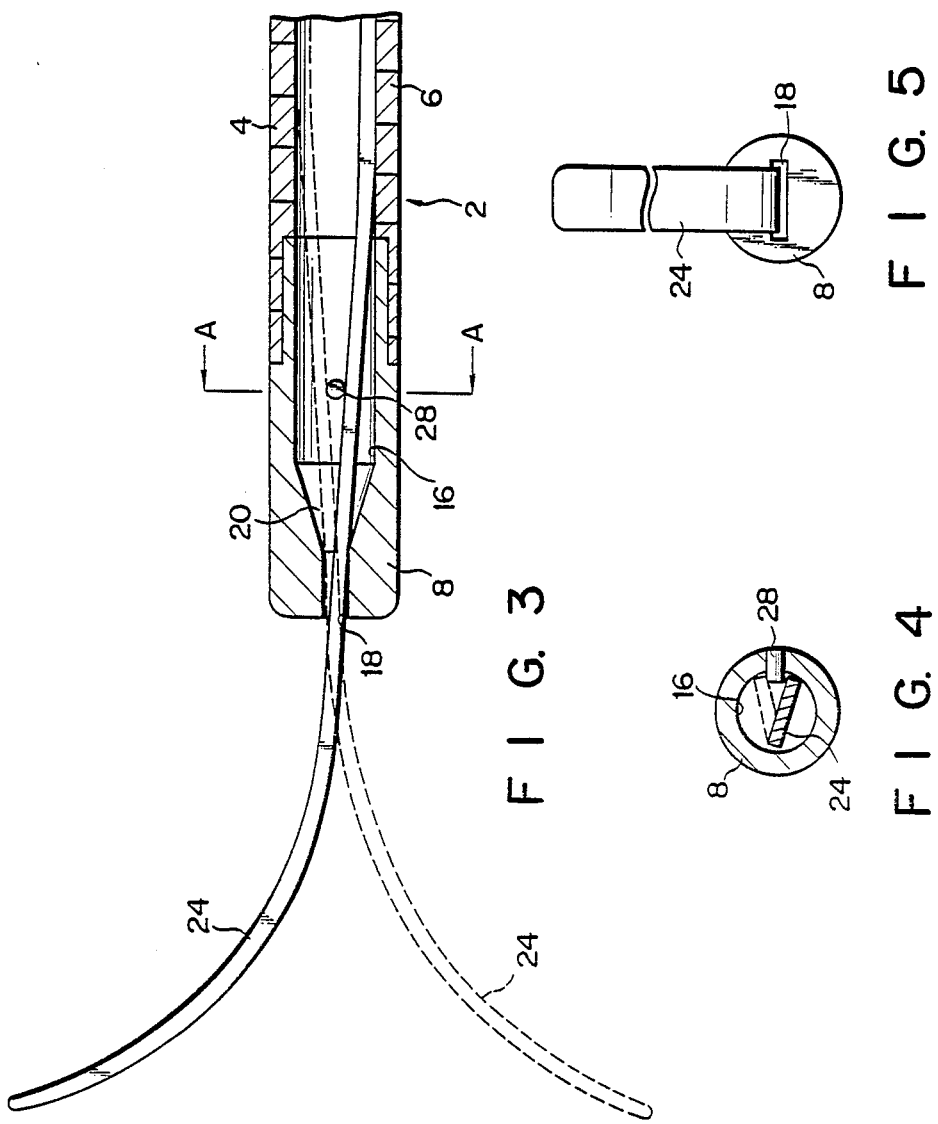

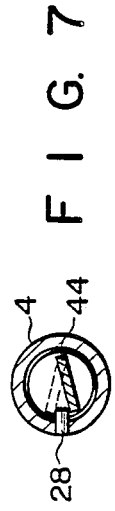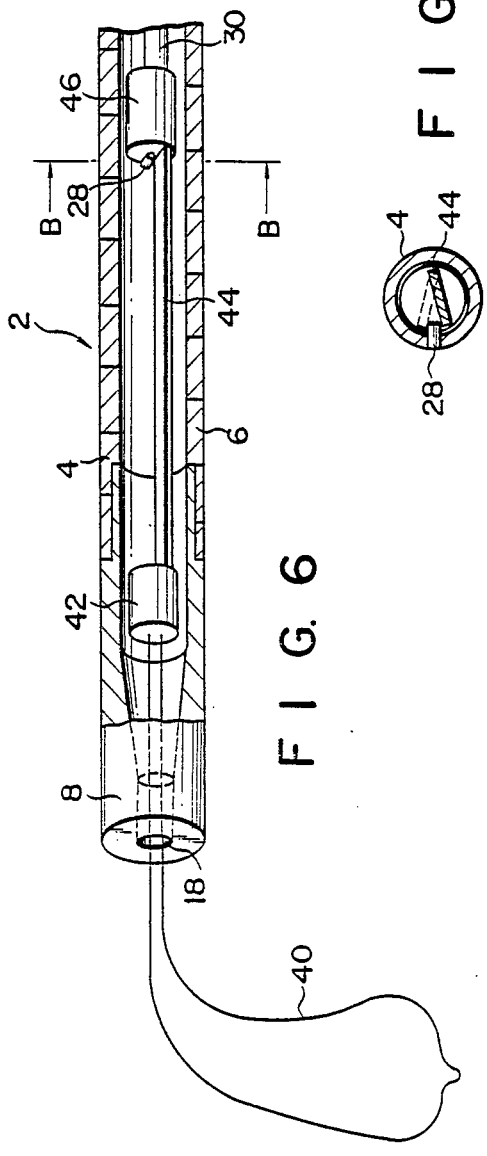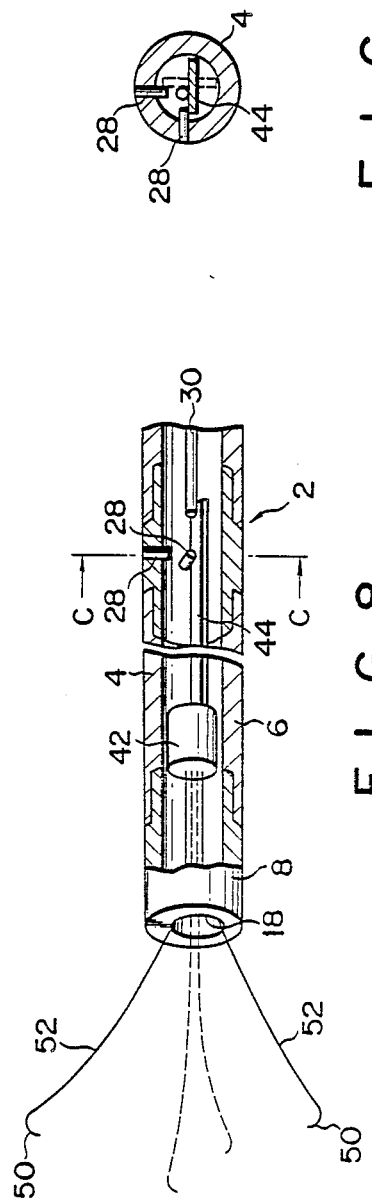

TREATING INSTRUMENT FOR USE WITH AN ENDOSCOPE

BACKGROUND OF THE INVENTION

1. Field of the Invention

This invention relates to a treating instrument for use with an endoscope, which is introduced through a channel of an endoscope into the body cavity to treat the diseased part.

2. Description of the Prior Art

Among known typical treating instruments for use with an endoscope are one disclosed in U.S. Pat. No. 4,190,942, another disclosed in Japanese Utility Model Disclosure No. 54-63989 and still another disclosed in Japanese Utility Model Publication No. 46-23833. Any of these treating instruments is introduced through the channel of an endoscope into the body cavity. While observing the treated part through an endoscope, the operator can handle the treating instrument to remove and recover foreign objects such as a calculus, for example, or to take samples of living tissue from the body.

A conventional treating instrument is provided at its distal end with a treating element such as a cup part or a holding part. The treating element of a conventional treating instrument has directionality that it can reach foreign objects such as a calculus or the tissue of the diseased part only from a specific direction. The insertion section of an endoscope that has been inserted into the body cavity is bent following the shape of the body cavity. Generally, the bent part at the distal end portion of the insertion section is bent toward the treated part.

When a conventional treating instrument is inserted into the channel of an endoscope which is bent as described above, it is no easy matter to direct the distal end or the treating element of the instrument to a direction suitable for treatment of a calculus, for example, The direction of the distal end of the treating instrument can be changed by rotating the whole body of the endoscope. However, there is a possibility of losing sight of the object in rotating the endoscope. Also, the distal end of the treating instrument can be rotated by rotating the operating section of the instrument. However, when the operating section is rotated, there is a problem that the operating section and the distal end of the treating instrument do not rotate with exactly the same rotating angle due to the friction between the external circumferential surface of the intermediate part and the internal circumferential surface of the channel of the endoscope. When the operating section is rotated while observing the position of the distal end or the treating element of a treating instrument, the whole treating instrument often turns around, reverting to its former position in an instant.

As has been described, when a conventional treating instrument for use with an endoscope is used in the body cavity, it is difficult to set the direction of the distal end of the treating element readily, accurately and quickly during its use. For this reason, a long time has been required for treatment of the patient and a burden on the patient as well as on the doctor has been very great.

SUMMARY OF THE INVENTION

The present invention has been made in consideration of the above problem and has as its object to provide a treating instrument for use with an endoscoped which allows the direction of a treating element having directionality to be set readily, quickly and accurately.

In order to achieve the above object, a treating instrument for use with an endoscope comprises:

a flexible sheath having an opening at its distal end portion;

a treating element having directionality and accommodated slidably in the sheath and being capable of extending through the opening of the sheath and being used from specific directions to reach the treated part;

an elongated member connected at its one end portion to the proximal end portion of the treating element and inserted slidably in the sheath;

operating means attached to the other end portion of the elongated member, arranged at the rear of the proximal end portion of the sheath and used to move forward and backward and rotate the treating element; and stopping means for limiting the rotating angle of the treating element when the treating element is rotated by the operating means.

With this treating instrument of this invention, for use with an endoscope, it is possible to direct a treating element having directionality of being used only in a specific direction to a correct direction toward the treated part easily. As a result, the operability of a treating instrument can be improved, time required for treatment of the diseased part and consequently, the burden on the patient and the doctor can be lightened.

Brief Description of the Drawings

FIGS. 1 and 3 are longitudinal sectional views of the distal end portion of a treating instrument according to the first embodiment of this invention, for use with an endoscope;

FIG. 2 is a side view partially in cross section showing an endoscope and a treating instrument according to the first embodiment incorporated in the endoscope, inserted in the body cavity;

FIG. 4 is a transverse sectional view taken along line A—A of FIG. 3;

FIG. 5 is a front view of the treating instrument of FIG. 3;

FIG. 6 is a longitudinal sectional view of the distal end of a treating instrument according to the second embodiment of this invention, for use with an endoscope;

FIG. 7 is a transverse sectional view taken along line B—B of FIG. 6;

FIG. 8 is a longitudinal sectional view of a treating instrument according to the third embodiment of this invention, for use with an endoscope;

FIG. 9 is a transverse sectional view taken along line C—C of FIG. 8;

DETAILED DESCRIPTION OF THE PREFERRED EMBODIMENTS

Figure 10:
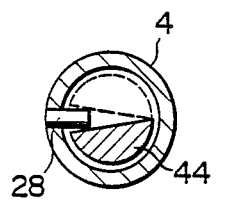
FIGS. 10 to 12 are transverse sectional views, showing three modifications of the plate used in the second and third embodiments.

Embodiments of this invention will now be described with reference to the accompanying drawings.

FIGS. 1 to 5 show various views of a treating instrument for an endoscope in a first embodiment of this invention. As shown in FIG. 1, treating instrument 2 for use with an endoscope has sheath 4. Sheath 4 comprises flexible closely-wound coil 6 and tip 8 coupled to the distal end of coil 6. As shown in FIG. 2, sheath 4 is at its proximal end fitted with mouthpiece 14. When in use, sheath 4 flexible from the distal end to the proximal end, is inserted into inserting channel 12 of endoscope 10.

Tip 8 has in its rear portion internal hole 16 which is circular in cross section and in its distal end opening 18 which is rectangular in cross section. Formed between opening 18 and internal hole 16 is taper hole 20 having a sloped surface. The internal surfaces of internal hole 16, taper hole 20 and opening 18 continue smoothly, Treating element 24 is accommodated in continuous passage 22 formed in tip 8 and closely-wound coil 6.

Operating handle 26 to operate treating instrument 24 is connected to the proximal end of elongated member 30 and the distal end of elongated member 30 is connected to the proximal end of treating element 24. The proximal end of elongated member 30 with operating handle 26 extend outwards from mouthpiece 14. Mouthpiece 14 has locking bolt 32. By tightening or loosening locking bolt 32, elongated member 30 can be secured to or freed from mouthpiece 14. When locking bolt 32 has been loosened, elongated member 30 can be rotated and moved forward and backward by manipulating operating handle 26.

Treating element 24 is formed of a belt-shaped plate with two wide surfaces across the width. This belt-shaped plate is configured such that it can gently bend in a direction perpendicular to either one of the two surfaces. The overall length of treating element 24 is set such that the distal end of treating element 24 is capable of extending for a specified distance from pin 28 when operating handle 26 is pushed deepest. When the distal end of treating element 24 is extended outwards through opening 18, the distal end of treating element 24 bends in either of the two directions indicated by a solid line and a dotted line in FIG. 3.

Referring to FIG. 4, a piece of pin 28 for restricting rotation projects in internal hole 16 of tip 8. When the width of treating element 24 is almost equal to the inside diameter of internal hole 22, the projecting length in sheath 4 of rotation-restricting pin 28 is adjusted to be shorter than the radius of internal hole 22. The purpose of this adjustment is not to hinder the rotation of treating element 24 when the treating element is rotated about 180 degrees or about a half of one rotation.

How to use the treating instrument according to this invention, for use with an endoscope will now be described with reference to FIG. 2. As shown in FIG. 2, to begin with, tip 8 and sheath 4 of treating instrument 2 are introduced into body cavity 34 through inserting channel 12 of endoscope introduced in advance into body cavity 34. Then, treating element 24 is fixed by means of locking bolt 32 under the condition that treating element is drawn into closely-wound coil 6 of sheath 4 and tip 8.

Next, the distal end of treating instrument 2 is introduced near a treated part where there is calculus 36, for example, and elongated member 30 is freed by loosening locking bolt 32. Elongated member 30 is pushed forward by manipulating operating handle 26, thereby projecting the distal end of treating element 24 a little from opening 18, At this time, if treating element 24 is bent in a direction suited for treating calculus 36, treating element 24 can be pushed ahead without changing its direction.

When treating element 24 is made to project a little from opening 18, if treating element 24 is bent in a direction unsuitable for treating calculus 36, elongated member 30 is withdrawn to bring treating element 24 into internal hole 22 of tip 8. Then, elongated member 30 is rotated clockwise by means of operating handle 26. By this rotation, treating element 24 rotates from the position indicated by the solid line to the position indicated by the dotted line as shown in FIG. 4 and comes into contact with rotation-restricting pin 28. To be more specific, treating element 24 is rotated about a half rotation, namely, about 180 degrees. If elongated member 30 is moved forward through sheath 4 under the condition after rotation, treating element 24 passes taper hole 20 and projects from opening 18 of a rectangular cross section. In this manner treating element 24 comes into a condition suitable for treatment of calculus 36.

Then, the distal end of treating element 24 is inserted gradually between calculus 36 and the mucous membrane of body cavity 34. When the distal end of treating element 24 has passed calculus 36, locking bolt 32 is tightened to fix elongated member 30. Put otherwised when treating element 24 projects ahead of calculus 36, treating element 24 is fixed.

Next, sheath 4 of treating instrument 2 is pulled out of inserting channel 12 of endoscope 10 or the whole of treating instrument 2 is drawn out from body cavity 34 together with endoscope 10, thereby moving calculus 36 toward the opening of body cavity 34.

As set forth above, with this treating instrument according to this invention, for use with an endoscope, the direction of treating element 24 can be changed easily according to the condition of the treated object, Thus, the treating instrument can be used by directing it in a position suitable for treatment of the affected part.

A second embodiment of a treating instrument according to this invention, for use with an endoscope, will now be described with reference to FIGS. 6 and 7. This second embodiment relates to the improvement of a high frequency snare assembly which uses a high frequency current to treat the affected part.

As shown in FIG. 6, treating instrument 2 includes sheath 4, tip 8 and snare wire 40 which serves as a treating element. Snare wire 40 has directionality for bending in a specified direction. The proximal end of snare wire 40 is connected to a first connecting member 42 movably accommodated in sheath 4. First connecting member 42 is coupled to the distal end of elongated plate, or bar-shaped member, 44. The proximal end of plate 44 is coupled to a second connecting member 46. Second connecting member 46 has elongated member 30 coupled thereto and to the proximal end of elongated member 30, operating handle 26 is attached just as in the first embodiment. Therefore, by rotating operating handle 26, second connecting member 46, plate 44 and first connecting member 42 are rotated and thereby snare wire 40 can be rotated simultaneously.

Rotation-restricting pin 28 is attached to the wall of sheath 4 between first connecting member 42 and second connecting member 46. This rotation-restricting pin 28 prevents the rotation of plate 44 just as in the first embodiment. When plate 44 is moved forward or backward, rotation-restricting pin 28 contacts first connecting member 42 or second connecting member 46. In this way, the longitudinal travel range of plate 44 is defined. As shown in FIG. 6, when elongated member 30 is pushed forward to let snare wire 40 project from opening 18 of tip 8, rotation-restricting pin 28 abuts against second connecting member 46 and the forward movement is stopped. At this time, snare wire 40 projects for the maximum projecting length, forming the largest loop. On the other hand, when elongated member 30 is pulled to bring snare wire 40 into tip 8 from opening 18 thereof, rotation-restricting pin 28 abuts against first connecting member 42 and the withdrawal movement is stopped. At this time, snare wire 40 has reached the set storing position.

How to use the treating instrument of the second embodiment will now be described in the following. Just as in the first embodiment, first of all, tip 8 and sheath 4 of treating instrument 2 are introduced into the body cavity and the distal end of tip 8 is positioned near the part to be treated. And elongated member 30 is freed by loosening locking bolt 32.

Then, elongated member 30 is pushed forward by manipulating operating handle 26 to let snare wire 40 as a treating element project from 18 of tip 8. At this time, if the bent direction of snare wire 40 is suitable for treatment of the patient, treatment by high-frequency current can be performed with snare wire 40 applied to a polyp, for example, by manipulating operating handle 26.

On the other hand, when the distal end of snare wire 40 is made to project from opening 18 of tip 8, if the bent direction of snare wire 40 is not suitable for treatment, elongated member 30 is rotated clockwise by manipulating operating handle 26. By this rotation, plate 44, together with snare wire 40, is rotated in sheath 4 from the position indicated by the solid line to the position indicated by the dotted line as shown in FIG. 7. In this rotating operation, plate 44 comes into contact with rotation-restricting pin 28 and is rotated about a half rotation, that is, about 180 degrees. Consequently, as in the first embodiment, the snare wire can be bent to a desired direction.

A holding forceps may be used in place of snare wire 40 in the second embodiment. First connecting member 42 is coupled by plate 44 to second connecting member 46, but some other connecting member may be used in place of plate 44.

FIGS. 8 and 9 show views of a treating instrument as a third embodiment of this invention. This third embodiment relates to the improvement of a holding forceps as a treating instrument for use with an endoscope.

As shown in FIG. 8, holding forceps 2 comprises a pair of holding wires 52 which serve as treating elements, each holding wire 52 having claw 50 at its end. A pair of holding wires 52 are connected to first connecting member 42, which is then connected with plate 44 and elongated member 30 just as in the second embodiment. However, second connecting member 46 is not used in this embodiment. Two rotation-restricting pins 28 are fastened to the wall of sheath 4 at the rear of connecting member 42. When holding wires 52 are pulled into the interior from opening 18 of tip 8, first connecting member 42 comes into contact with rotation-restricting pin 28 and stops. At this time, holding wires 52 have reached the set storing position.

In the treating instrument of the third embodiment, two rotation-restricting pins are fastened to sheath 4, the pins being separated about 90 degrees from each other as shown in FIGS. 8 and 9. As a result, plate 44 can be placed in either of the two intersecting positions as indicated by the solid line and the dotted line in FIG. 9. Consequently, the position of holding wires 52 can be changed to the other one of the two intersecting positions when necessary.

Figure 11:
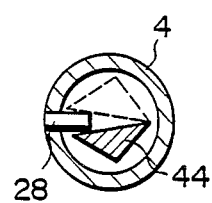
Figure 12:
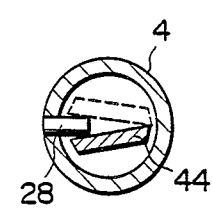

FIG. 10 to 12 show three modifications of plate 44 used in the second and third embodiments. The plate of FIG. 10 has a semicircular cross section. The plate of FIG. 11 has a triangular cross section. The plate shown in FIG. 12 has a trapezoidal cross section. In this invention, the cross section of plate 44 is not limited to a rectangular one. Any plate can be used as plate 44 if it has a contact surface which abuts on pin 28 when the instrument is rotated, thereby to allow the instrument to rotate by an angle falling within a specific range. It is desired that the contact surface be flat and have a width less than the inside diameter of sheath 4.

The various plates shown in FIGS. 10 to 12 can be used in the first embodiment. When any one of these plates is used in place of treating element 24 which has a rectangular cross section, opening 18 of tip 8 must have a shape identical to the cross section of treating element 24, or such a shape as will allow the passage of treating element 24.

Figure 13:
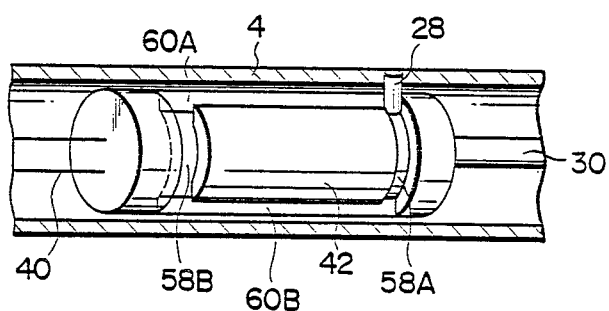
FIG. 13 is a perspective view, showing an modification of the first connecting member used in the second and third embodiments.

FIG. 13 shows a modification of the first connecting member used in the second and third embodiments. This modification has two grooves 58A and 58B cut in the end portions and extending, half around the connection member. It also has two longitudinal grooves 60A and 60B. Groove 60A communicates with the corresponding ends of grooves 58A and 58B, and groove 60B communicates with the other ends of groove 58A and 58B. Grooves 58A, 58B, 60A and 60B form a looped guide groove. Rotation-restricting pin 28 is inserted in this guide groove. Hence, first connecting member 42 shown in FIG. 13, which has grooves 58A, 58B, 60A and 60B, functions as a cam.

When first connecting member 42 (FIG. 13) is moved forward, pin 28 is guided in any longitudinal groove 60A or 60B until it abuts on the wall of groove 58A. When member 42 (FIG. 13) is moved backward, pin 28 is guided in longitudinal groove 60A or 60B until it abuts on the wall of groove 58B. Therefore, member 42 can move in its axial direction, only for the distance equal to the length of either longitudinal groove.

Wherever pin 28 moves from either longitudinal groove into groove 58A or 58B, member 42 can be rotated about 180°. In the condition shown in FIG. 13, member 42 can be rotated counterclockwise through 180°. In this case, pin 28 then moves into longitudinal groove 60B, and member 42 can be moved in its axial direction.

When the modification of first connecting member 42 is used in the third embodiment, grooves 58A and 58B must be cut and extend around member 42 such that member 42 can be rotated about 90°. In this case, when member 42 is rotated about 90°, holding wire 52 can extend in one of two directions perpendicular to each other.

What is claimed is:

1. A treating instrument for use with an endoscope, comprising;
   a flexible sheath having a distal end portion and a proximal end portion, said sheath having an opening formed at the distal end portion;
   a treating element having a distal end portion and a proximal end portion and accommodated slidably in said sheath, said treating element having directionality and being capable of extending through the opening of said sheath and being used from specific directions to reach the treated part;

an elongated member connected at its one end portion to the proximal end portion of said treating element and inserted slidably in said sheath;

operating means attached to the other end portion of said elongated member, arranged at the rear of the proximal end portion of said sheath and used to move forward and backward and rotate said treating element; and stopping means for limiting the rotating angle of said treating element when said treating element is rotated by said operating means.

2. The treating instrument according to claim 1 wherein said stopping means is attached to the distal end portion of said sheath and has a pin protruding into said sheath, and said treating element has a contact surface on which said pin abuts when said treating element is rotated.

3. The treating instrument according to claim 2, wherein said contact surface is flat.

4. The treating instrument according to claim 3, wherein said treating element has a substantially polygonal cross section.

5. The treating instrument according to claim 3, wherein said treating element has a substantially semicircular cross section.

6. The treating instrument according to claim 2, wherein said treating element is a belt-shaped plate having a property of bending in a specific direction.

7. The treating instrument according to claim 6, wherein said sheath is provided with a tip member having an internal hole and said opening, said opening having a substantially polygonal cross section, said internal hole having a substantially circular cross section, said tip member having between said opening and said internal hole a taper hole for communication of said opening with said internal hole.

8. The treating instrument according to claim 1, further comprising:

a bar-shaped member having one end portion connected to the proximal end portion of said treating element and the other end portion connected to said elongated member, the bar-shaped member cooperating with said stopping means to limit the rotating angle of said treating element to a predetermined range when said treating element is rotated.

9. The treating instrument according to claim 8, wherein said bar-shaped member has a substantially polygonal cross section.

10. The treating instrument according to claim 8, wherein said bar-shaped member has a substantially semicircular cross section.

11. The treating instrument according to claim 8, further comprising:

a first connecting member mounted between the proximal end portion of said treating element and one end portion of said bar-shaped member, the connecting member cooperating with said stopping means to limit the distance for said treating element to retract in said sheath.

12. The treating instrument according to claim 11, wherein said treating element comprises a holding tool having two claws opposedly disposed.

13. The treating instrument according to claim 11, further comprising:

a second connecting member mounted between one end portion of said elongated member and the other end portion of said bar-shaped member, the second connecting member cooperating with said stopping means to limit the distance for said treating element to extend from the opening of said sheath.

14. The treating instrument according to claim 13, wherein said treating element comprises a snare wire having a property of bending in a specified direction.

15. The treating instrument according to claim 1, further comprising:

a columnar member mounted between the proximal end portion of said treating element and one end portion of said elongated member, said columnar member cooperating with said stopping means when it is rotated, thereby to limit an angle through which said treating element is allowed to rotate.

16. The treating instrument according to claim 15, wherein said columnar member has a groove extending in its circumferential direction for a predetermined distance, and said stopping means has a pin protruding into said sheath and being inserted in the groove of said columnar member.

17. The treating instrument according to claim 16, wherein said columnar member has a longitudinal groove extending in its axial direction from one end of said groove for a predetermined distance, said longitudinal groove being able to guide the pin of said stopping means so that said treating member is able to slide in its axial direction within said sheath.

* * * * *